United States Patent
Ackerman et al.

(10) Patent No.: US 8,772,196 B2
(45) Date of Patent: *Jul. 8, 2014

(54) AROMATICS HYDROGENATION CATALYST AND A METHOD OF MAKING AND USING SUCH CATALYST

(75) Inventors: Russell Craig Ackerman, Katy, TX (US); Christian Gabriel Michel, Houston, TX (US); John Anthony Smegal, Houston, TX (US); Johannes Anthonius Robert Van Veen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1215 days.

This patent is subject to a terminal disclaimer.

(21) Appl. No.: 12/197,386

(22) Filed: Aug. 25, 2008

(65) Prior Publication Data

US 2009/0062582 A1 Mar. 5, 2009

Related U.S. Application Data

(60) Provisional application No. 60/968,129, filed on Aug. 27, 2007.

(51) Int. Cl.
| | | |
|---|---|---|
| *C07C 5/02* | (2006.01) | |
| *B01J 35/10* | (2006.01) | |
| *B01J 37/00* | (2006.01) | |
| *C10G 45/46* | (2006.01) | |
| *B01J 21/12* | (2006.01) | |
| *B01J 35/02* | (2006.01) | |
| *B01J 23/44* | (2006.01) | |
| *C07C 5/10* | (2006.01) | |
| *C10G 45/52* | (2006.01) | |
| *B01J 23/42* | (2006.01) | |

(52) U.S. Cl.
CPC .............. *B01J 21/12* (2013.01); *B01J 35/1042* (2013.01); *B01J 23/42* (2013.01); *B01J 37/0009* (2013.01); *B01J 35/1047* (2013.01); *C10G 45/46* (2013.01); *B01J 35/023* (2013.01); *B01J 35/1066* (2013.01); *C10G 2300/1096* (2013.01); *B01J 23/44* (2013.01); *C07C 5/10* (2013.01); *C07C 2523/44* (2013.01); *B01J 35/1061* (2013.01); *C10G 45/52* (2013.01); *B10J 35/1019* (2013.01)

USPC ........... 502/263; 502/210; 502/213; 502/204; 502/206; 502/207; 502/211; 502/325; 208/111.3; 585/266; 585/664

(58) Field of Classification Search
CPC ............ B01J 21/12; B01J 23/42; B01J 23/44; B01J 35/023; B01J 35/1019; B01J 35/1061; B01J 35/1042; B01J 35/1047; B01J 37/0009; C07C 5/10; C07C 2523/44; C10G 45/52; C10G 2300/1096
USPC ......... 502/325, 258, 204, 206, 207, 210, 211, 502/213, 263; 525/333.3
IPC .................................................. C07C 5/23, 5/25
See application file for complete search history.

(56) References Cited

U.S. PATENT DOCUMENTS

| | | | |
|---|---|---|---|
| 3,637,484 A | 1/1972 | Hansford | 208/143 |
| 3,684,688 A * | 8/1972 | Roselius | 208/50 |
| 3,943,053 A | 3/1976 | Kovach et al. | 208/143 |
| 4,289,653 A | 9/1981 | Jaffe | 252/453 |
| 4,499,197 A | 2/1985 | Seese et al. | 502/65 |
| 4,849,093 A | 7/1989 | Vauk et al. | 208/143 |
| 4,988,659 A | 1/1991 | Pecoraro | 502/235 |
| 5,225,383 A | 7/1993 | Kukes et al. | 502/66 |
| 5,308,814 A | 5/1994 | Kukes et al. | 502/66 |
| 5,468,368 A * | 11/1995 | Baker et al. | 208/58 |
| 6,296,759 B1 | 10/2001 | Vaarkamp et al. | 208/217 |
| 6,872,685 B2 | 3/2005 | Timken | 502/263 |
| 6,995,112 B2 | 2/2006 | Timken et al. | 502/240 |
| 8,278,241 B2 * | 10/2012 | Ackerman et al. | 502/263 |
| 2002/0160911 A1 * | 10/2002 | Benazzi et al. | 502/240 |
| 2003/0060582 A1 | 3/2003 | Percoraro et al. | 526/129 |
| 2004/0065587 A1 | 4/2004 | Collin et al. | 208/89 |
| 2004/0199040 A1 * | 10/2004 | Hoek et al. | 585/664 |
| 2005/0197249 A1 | 9/2005 | Creyghton et al. | 502/439 |
| 2005/0228143 A1 * | 10/2005 | Yamakawa et al. | 525/333.3 |

FOREIGN PATENT DOCUMENTS

| | | | | |
|---|---|---|---|---|
| WO | WO9410263 | 5/1994 | | C10G 45/60 |
| WO | WO2007031560 | 3/2007 | | B01J 21/02 |

* cited by examiner

*Primary Examiner* — Jun Li
(74) *Attorney, Agent, or Firm* — Charles W. Stewart

(57) ABSTRACT

Disclosed is a composition useful in the saturation of aromatics contained in a hydrocarbon feedstock. The composition includes a support composition having a high macroporosity of greater than 51 percent. The support composition comprises an amorphous silica-alumina having unique properties.

15 Claims, No Drawings

AROMATICS HYDROGENATION CATALYST AND A METHOD OF MAKING AND USING SUCH CATALYST

This application claims the benefit of U.S. Provisional Application Ser. No. 60/968,129, filed Aug. 27, 2007.

The present invention relates to a high macroporosity support composition containing amorphous silica-alumina, an aromatics hydrogenation catalyst that includes a noble metal supported on the high macroporosity support composition, and methods of making and using such high macroporosity support composition and aromatics hydrogenation catalyst.

In many instances, various of the refinery streams have concentrations of aromatics and often require further processing in order to provide a product having required or desired characteristics and properties. It is recognized that the removal of aromatics contained in diesel fuel can contribute to a desirable increase in its cetane number and that the removal of aromatics contained in jet fuel can contribute to an improvement in its smoke point. The viscosity properties of solvent and lubricating oils can also be improved by the removal of aromatics from these oils.

One early patent, U.S. Pat. No. 3,637,484, discloses a catalyst composition comprising platinum and/or palladium deposited on a heterogeneous support that includes a silica-alumina coprecipitate or cogel. The heterogeneous support has a high pore volume with a substantial portion of this pore volume being in the pores having a diameter greater than 500 Å. The silica-alumina cogel that is dispersed in the alumina gel matrix of the heterogeneous support, however, need not exhibit the large pore structure as required for the overall catalyst composite.

U.S. Pat. No. 3,943,053 discloses a process for aromatics hydrogenation using a catalyst comprising platinum and palladium on an inert oxide support. The inert oxide support is a high surface area alumina and is preferred over acidic materials such as silica-alumina. The final calcined catalyst contains from 0.3 to 0.5 wt. % platinum metal and from 0.3 to 0.9 wt. % palladium metal.

Another catalyst that is used for the hydrogenation of aromatics contained in hydrocarbon distillate feedstock is disclosed in U.S. Pat. No. 5,308,814, which describes a catalyst comprising a hydrogenation component and a catalyst support. The catalyst support component comprises zeolite Y and a refractory inorganic oxide such as silica, alumina, or silica-alumina. The hydrogenation component of the catalyst may be platinum and palladium that is present in an amount ranging from about 0.1 wt. % to about 2.0 wt. % in a weight ratio of elemental palladium to elemental platinum in the range of from 10:1 to 1:10. The hydrogenation component can be deposited or incorporated upon the catalyst support by impregnation methods.

U.S. Pat. No. 6,296,759 discloses a catalyst that comprises platinum, palladium or a combination thereof on a non-crystalline, acidic silica-alumina support, which support is obtained by sol-gel techniques, and is useful in the hydrogenation of aromatic compounds contained in distillate feedstocks that also contain sulfur. The sol-gel technique includes the dropwise addition of an aqueous sol of inorganic salts of aluminum and silicon through an oil-phase to form beads. The formation of the beds makes the use of a separate shaping step, such as extrusion, not required.

WO 94/10263 discloses a catalyst useful in the preparation of lubricating base oils. The catalyst comprises a hydrogenation component supported on a carrier that includes amorphous silica-alumina, which carrier has a macroporosity in the range of from 5% vol. to 50% vol. The hydrogenation component may be selected from metals of Groups VIB and VIII of the Periodic Table. The carrier is preferably prepared by mulling a mixture of amorphous silica-alumina and a suitable liquid, extruding the mixture and then drying the resulting extrudates. The carrier may comprise a binder, and peptizing agents and extrusion aids may be used in the preparation of the carrier.

It is desirable to have a support composition useful in supporting a noble metal component to thereby form an aromatics hydrogenation catalyst composition.

It is also desirable to have a noble metal aromatics hydrogenation catalyst composition having a particularly good aromatics hydrogenation activity.

It is also desirable to have a process for the hydrogenation of aromatics that are contained in a hydrocarbon feedstock, and, in particular, a process for the saturation of aromatics contained in hydrocarbon distillate feedstocks such as jet fuel and diesel so as to improve the properties thereof.

Accordingly, provided is a composition, comprising: a support composition having a macroporosity greater than 51% and comprising amorphous silica-alumina. A noble metal may be incorporated into the support composition to thereby provide an aromatics hydrogenation catalyst. The support composition is prepared by agglomerating a mixture comprising water and amorphous silica-alumina and drying the resulting agglomerate to yield the support composition. Incorporated into the support composition is a noble metal selected from the group consisting of platinum, palladium and a combination thereof to thereby provide an impregnated support composition that may be calcined to provide an aromatics hydrogenation catalyst. The aromatics hydrogenation catalyst may be used for the hydrogenation of aromatics of a hydrocarbon feedstock containing a concentration of aromatics by contacting said hydrocarbon feedstock therewith under suitable aromatics hydrogenation conditions to yield a product having a reduced aromatics concentration.

The invention relates to a novel aromatics hydrogenation catalyst that has improved aromatics hydrogenation catalytic activity over comparative prior art aromatics hydrogenation catalysts and to a process for the dearomatization of hydrocarbon feedstocks, and, in particular, for the dearomatization of hydrocarbon distillates such as kerosene and diesel. The invention also relates to a novel support composition and method of making such support composition that may suitably be used as a support or carrier for at least one noble metal that is incorporated therein so as to provide a final catalyst composition, i.e., aromatics hydrogenation catalyst, of the invention. This support composition has unique physical properties that are believed to provide for a final catalyst composition having improved activity toward aromatics saturation.

The support composition is made using an amorphous silica-alumina having unique properties and which can be prepared by the novel, so-called pH swing method as fully described in co-pending provisional patent application No. 60/968122, filed concurrently with this application, entitled "An Amorphous Silica-Alumina Composition and a Method of Making and Using Such Composition," which disclosure is incorporated herein by reference. The support composition, thus, comprises amorphous silica-alumina that is characterized by having certain unique properties. The physical characteristics of the amorphous silica-alumina are believed to provide for a support composition having properties that make it particularly desirable for use in supporting or carrying at least one noble metal hydrogenation component, and, further, that impart certain catalytic benefits making the final catalyst composition highly active when used in certain applications. One particularly advantageous application for the use of the final catalyst composition is in the hydrogenation or saturation of aromatics that are contained in hydrocarbon distillates.

The amorphous silica-alumina used in the preparation of the support composition is highly amorphous in that it contains very little alumina that is crystalline. The amount of crystalline alumina in the amorphous silica-alumina is indicated by its characteristic powder X-ray diffraction (XRD) pattern that has a significant lack of XRD peaks which are representative of various of the crystalline alumina phases. Generally, the amount of alumina that is in the crystalline phase contained in the amorphous silica-alumina is less than 10 weight percent of the total weight of the amorphous silica-alumina. More specifically, the amorphous silica-alumina has less than 8 weight percent crystalline alumina, and, most specifically, it has less than 5 weight percent crystalline alumina.

The amorphous silica-alumina can have a silica content that is in the range of from 10 to 90 weight percent, with the weight percent being based on the total dry weight of the amorphous silica-alumina. The preferred silica content, however, is in the range of from 25 to 75 weight percent, and, most preferred, the silica content is in the range of from 40 to 60 weight percent. The alumina may be present in the amorphous silica-alumina in an amount in the range of from 10 to 90 weight percent, more specifically, from 25 to 75 weight percent, and, most specifically, from 40 to 60 weight percent.

A particularly important property of the amorphous silica-alumina is that it has a relatively high ratio of its pore volume that is contained in its large pores to its pore volume that is contained in its medium and small pores. One measure of this property is the ratio of the pore volume (cc/gm) contained in the pores of the amorphous silica-alumina having a pore diameter of less than 2150 Å ("A") to the pore volume contained in the pores of the amorphous silica-alumina having a pore diameter of less than 210 Å ("B"). This ratio of A-to-B (A/B ratio), in general, should exceed 2.2, and, preferably, the A/B ratio exceeds 2.4, and, most preferably, the A/B ratio exceeds 2.5.

References herein to total pore volume are to the pore volume as determined using the Standard Test Method for Determining Pore Volume Distribution of Catalysts by Mercury Intrusion Porosimetry, ASTM D 4284-88, at a maximum pressure of 4000 bar, assuming a surface tension for mercury of 484 dyne/cm and a contact angle with amorphous silica-alumina of 140°.

The amorphous silica-alumina has a significantly high surface area and total pore volume. Its surface area can be in the range of from 190 $m^2$/gm to 400 $m^2$/gm, but, more specifically, it is in the range of from 200 $m^2$/gm to 350 $m^2$/gm, and, more specifically, from 225 $m^2$/gm to 325 $m^2$/gm. The total pore volume of the amorphous silica-alumina is in the range of from 0.8 cc/gm to 1.3 cc/gm, more specifically, from 0.9 cc/gm to 1.2 cc/gm, and, most specifically, from 0.95 cc/gm to 1.1 cc/gm.

Another important property of the amorphous silica-alumina used in the preparation of the support composition is that it should have an Aluminum ($^{27}Al$) solid-state NMR spectrum that exhibits penta-coordination peak having a relative size to the other aluminum peaks representative of the presence of penta-coordinated aluminum in an amount greater than 30 percent of the total of the three types of aluminum represented by the three peaks of its NMR spectrum. More specifically, the strong penta-coordination peak of $^{27}Al$ solid-state NMR spectrum of the amorphous silica-alumina should be greater than 35% of the total of the three types of aluminum, and, most specifically, it should be greater than 40% of the total of the three types of aluminum.

As referenced herein, the NMR spectrum of the amorphous silica-alumina is that which is generated using any standard Solid-State Nuclear Magnetic Resonance (NMR) spectroscopy methodology known to those skilled in the art of using NMR techniques for characterizing structural configurations of solid materials. The determination of the NMR spectrum of the amorphous silica-alumina composition can be made by using any suitable instrumentation and equipment that provide a spectrum that is substantially similar to one which can be provided by using the NMR spectrometer manufactured and marketed by Varian, Inc of Palo Alto, Calif. as Varian 400-MR NMR spectrometer using a Doty Scientific, Inc. of Columbia, S.C., 5 mm high power solid-state NMR probe. Samples are loaded into a 5 mm silicon nitride ($Si_3N_4$) rotor and spun at 13 to 16 kHz (780,000 to 960,000 rpm) in a dry nitrogen atmosphere at room temperature. The stator housing is adjusted to be at a magic angle to the external magnetic field to minimize the broadening caused by random orientation of the individual nuclei with reference to the external magnetic field. The resonance frequency for aluminum nuclei at this field strength is 104.3 MHz. The spectral width of 0.5 MHz, a pulse width of 1.0 microsecond, and a recycle delay of 0.3 seconds are employed as the experimental conditions.

The aluminum solid-state NMR spectrum of the amorphous silica-alumina has three significant peaks: a first peak located at about 65 ppm on the chemical shift scale representing tetrahedral aluminum sites; a second peak located at about 30 ppm on the chemical shift scale representing penta-coordination aluminum sites; and a third peak located at about 3 to 6 ppm on the chemical shift scale representing octahedral aluminum sites. These chemical shifts are referenced to aqueous aluminum chloride at 0.0 ppm. The shifts of the aforementioned peaks can be influenced by the acidity and second order quadrupolar interaction experienced by the respective aluminum nuclei.

The support composition of the invention can be prepared by mixing the amorphous silica-alumina and a suitable liquid, such as water, forming the mixture into shaped particles, and, then drying the shaped particles. While the preferred support composition is made without the addition of a binder or an inorganic oxide material, an inorganic oxide material may, however, be mixed with the amorphous silica-alumina in the preparation of the support composition. Examples of inorganic oxide materials include silica, alumina, clays, magnesia, titania, and zirconia. Among these, silica and alumina are preferred.

If an inorganic oxide material is mixed with the amorphous silica-alumina to make the support composition, it can be present in an amount upwardly to 50% by weight of the support composition, and, suitably, from 5 to 30% by weight.

It is preferred to mix the starting materials, e.g. amorphous silica-alumina, or water, or an organic oxide, or a combination thereof, so as to provide a paste having properties making it capable of being extruded or formed into extrudate particles by any known extrusion method. Also, the amorphous silica-alumina and, if present, other starting materials may be agglomerated into shaped particles, such as, spheroids, pills or tablets, cylinders, irregular extrusions or merely loosely bound aggregates or clusters, by any of the methods known to those skilled in the art, including, but not limited to, molding, tableting, pressing, palletizing, extruding, and tumbling.

The drying of the shaped particle provides for the removal of certain quantities of water or volatiles that are included therein and may be conducted at any suitable temperature for removing excess water or volatiles. Preferably, the drying temperature will be in the range of from about 75° C. to 250° C. The time period for drying the shaped particle is any suitable time period necessary to provide for the desired amount of reduction in the volatile content of the shaped particle prior to incorporation of a hydrogenation component.

An essential property of the support composition is for it to have a high macroporosity. It is recognized that the properties of the amorphous silica-alumina used to make the support composition contribute to the support composition having such a high macroporosity. It is also believed that it is the high macroporosity of the support composition, and other properties, imparted to it by the amorphous silica-alumina used to make the support composition which provides for a final catalyst composition having a high aromatics hydrogenation activity.

The term "macroporosity" is used herein to refer to a measure of the porosity of the support composition as represented by the percentage of the total pore volume of the support composition that is contained in its macropores. The macropores are the pores of the support composition having a pore diameter greater than 350 angstroms (Å). The macroporosity of the support composition of the invention is exceptionally high in that the percentage of the total pore volume of the support composition that is contained in the macropores (i.e., pores having a pore diameter that is greater than 350 Å), or its macroporosity, is greater than 51 percent (%). Preferably, the macroporosity of the support composition is greater than 52%, and, more preferably, the macroporosity of the support composition is greater than 54%. An upper limit for the macroporosity of the support composition is less than 90%, or less than 80%, or even less than 70%.

It can also be important for the macropores of the support composition, when it is used in certain applications, to have somewhat of a narrow pore size distribution, and it is recognized that the unique properties of the amorphous silica-alumina used in the preparation of the support composition can provide for such a narrow pore size distribution. Indeed, it is due to certain of the unique properties of the amorphous silica-alumina that is made by the aforementioned pH swing method that enables the preparation of the support composition of the invention having the high macroporosity, as earlier described, and the narrow pore size distribution of the macropores. It is desirable for the percentage of the total pore volume of the support composition contained in its macropores having a pore diameter in the range of from 350 Å to 2000 Å to be greater than 40%, preferably, greater than 44%, and, most preferably, greater than 46%.

Concerning the total pore volume of the support composition that is contained in the extra-large macropores that have a pore diameter of greater than 5000 Å, it is desirable for the percentage of the total pore volume contained in such extra-large macropores to be less than 4%, preferably, less than 2%, and, most preferably, less than 1%.

Another desirable property of the support composition is for it to have a significant mesoporosity. The term "mesoporosity" is used herein to refer to a measure of porosity of the support composition as represented by the percentage of the total pore volume of the support composition that is contained in its mesopores. Additionally, it is important for a small proportion of the total pore volume of the support composition to be contained in the smaller pores thereof but with the support composition to have a reasonably large portion or percentage of its total pore volume that is contained in the mesopores, or, in other words, for the support composition to have a significant mesoporosity. The mesopores, as the term is used herein, are those pores of the support composition having a pore diameter in the range of from 50 Å to 350 Å. It is desirable for the mesoporosity of the support composition to be greater than 30%, preferably, greater than 35%, and, most preferably, greater than 40%.

The percentage of the total pore volume of the support composition contained in its smaller pores having a pore diameter of less than 70 Å should be less than 10% of the total pore volume of the support composition, preferably, less than 7%, and, most preferably, less than 5%.

Another characteristic of the support composition is that it has a significantly high surface area and total pore volume. Its surface area can be in the range of from 150 m$^2$/gm to 400 m$^2$/gm, but, more specifically, it is in the range of from 175 m$^2$/gm to 350 m$^2$/gm, and, more specifically, from 200 m$^2$/gm to 325 m$^2$/gm. The total pore volume of the support composition is in the range of from 0.8 cc/gm to 1.3 cc/gm, more specifically, from 0.9 cc/gm to 1.2 cc/gm, and, most specifically, from 0.95 cc/gm to 1.1 cc/gm.

To prepare the final catalyst composition of the invention, a noble metal component is incorporated into the support composition. The noble metal component can be incorporated into the support composition by using any of the suitable means or methods known to those skilled in the art for incorporating a noble metal into a catalyst support. It is preferred to use an impregnation method to incorporate the noble metal component into the support composition, and, among these methods, it is preferred to incorporate the noble metal component into the support composition using the well known incipient wetness method.

The impregnation solution of the noble metal solution comprises a heat-decomposable salt of platinum or of palladium, or of both platinum and palladium, dissolved in water. Examples of possible platinum salts that may be used include the platinum compounds of: chloroplatinic acid; ammonium chloroplatinate; bromoplatinic acid; platinum trichloride; platinum tetrachloride hydrate; platinum dichlorocarbonyl dichloride; dinitrodiaminoplatinum; sodium tetranitroplatinate and tetraammine platinum(II) nitrate. Examples of possible palladium salts that may be used include the palladium compounds of: chloropalladic acid; palladium chloride; palladium nitrate; palladium sulfate; diamine palladium hydroxide; tetraammine palladium chloride and tetraammine palladium(II) nitrate. The preferred platinum compound and palladium compound for use in the impregnation solution are, respectively, tetraammine platinum(II) nitrate and tetraammine palladium(II) nitrate.

The amount of noble metal incorporated into the support composition should be such as to provide the final catalyst composition of the invention having a noble metal content that is in the range of from 0.01 wt. % to 5 wt. % for each of the noble metals with the weight percent being based on the total weight of the final catalyst composition and calculated as elemental metal. The preferred noble metal content for each noble metal component is in the range of from 0.1 wt. % to 4 wt. %, and, most preferred, from 0.2 to 3 wt. %.

While the final catalyst composition may include either a platinum noble metal component or a palladium metal component, or both a platinum and a palladium noble metal component, it should be recognized that the use of a combination of the two noble metals contained in the final catalyst composition can provide enhanced aromatics hydrogenation activity. Thus, it is preferred for the final catalyst composition of the invention to comprise both a platinum component and a palladium component. In the preferred final catalyst composition, the weight ratio of elemental palladium-to-platinum is in the range of from 1:10 to 10:1, preferably, from 1:2 to 5:1, and, most preferably, from 1:1 to 3:1.

The support composition that is impregnated with the noble metal component is dried at any suitable temperature for removing excess water or volatiles therefrom. Generally, the drying temperature will be in the range of from about 75° C. to 250° C. The time period for drying the intermediate catalyst composition is any suitable time period necessary to provide for the desired amount of reduction in the volatile content and can be in the range of from 0.1 hour to 72 hours. After drying, the impregnated support composition is then calcined in the presence of an oxygen-containing fluid, such as air, at a temperature and for a time period that is suitable for achieving the desired degree of calcination to provide the final catalyst composition (aromatics hydrogenation catalyst). Generally, the calcination temperature is in the range of from 250° C. (482° F.) to 550° C. (1022° F.). The preferred calcination temperature is in the range of from 280° C. (536° F.) to 520° C. (968° F.).

The final catalyst composition of the invention generally has a surface area in the range of from 175 $m^2$/gm to 600 $m^2$/gm, as determined by the BET method employing $N_2$, preferably, from 200 $m^2$/gm to 550 $m^2$/gm, and, most preferably, from 225 $m^2$/gm to 500 $m^2$/gm. The pore volume of the final catalyst composition as determined by using standard mercury porosimety methodology is generally in the range of from 0.7 ml/gm to 1.3 ml/gm, and the median pore diameter of the final catalyst composition is in the range of from 50 angstroms (Å) to 250 angstroms.

The final catalyst composition of the invention is particularly useful in processes for the hydrogenation of aromatic hydrocarbons, and, especially, it is useful for the dearomatization of aromatics-containing hydrocarbon feedstocks. One contemplated hydrocarbon feedstock of the invention includes a refinery distillate stream comprising hydrocarbons having boiling temperatures at atmospheric pressure in the range of from about 140° C. (284° F.) to about 410° C. (770° F.). These temperatures are approximate initial and final boiling temperatures of the distillate feedstock.

Examples of the refinery streams intended to be included within the meaning of the term refinery distillate stream or distillate feedstock include straight run distillate fuels boiling in the referenced boiling range, such as kerosene, jet fuel, light diesel oil, heating oil, and heavy diesel oil, and the cracked distillates, such as FCC cycle oil, coker gas oil, and hydrocracker distillates.

Another contemplated hydrocarbon feedstock of the invention includes a refinery heavy oil fraction having a boiling range that at least in part overlaps the lubricating base oil boiling range. The source of the refinery heavy oil fraction may be a light or heavy vacuum gas oil derived from the vacuum distillation of an atmospheric residue fraction obtained by the atmospheric distillation of a crude oil. The boiling range of such vacuum gas oil is generally from 300° C. (572° F.) to 620° C. (1148° F.).

Prior to its use in the inventive process, the refinery heavy oil fraction may be processed by known hydrocracking and dewaxing, e.g. solvent dewaxing and catalytic dewaxing, process steps so as to provide a product having various of the desired properties for a lubricating base oil. The inventive process may include the processing of the refinery heavy oil fraction that has already been treated by process steps such as hydrocracking and dewaxing or the processing of the refinery heavy oil that has not undergone prior treatment. In the treating of the refinery heavy oil fraction, it is preferred to use the final catalyst composition of the invention as a catalyst for hydrofinishing a lubricating base oil feedstock having a boiling range of from 350° C. (662° F.) to 580° C. (1076° F.) and which is a refinery heavy oil fraction having been hydrotreated and dewaxed.

One embodiment of the inventive process involves the hydrogenation removal of aromatics compounds that are in the hydrocarbon feedstock in order to provide or yield a product having a reduced concentration of aromatics as compared to the concentration of aromatics in the hydrocarbon feedstock. In such a dearomatization process, the hydrocarbon feedstock may include an aromatics concentration in the range of from 1 wt. % to 80 wt. %, with the weight percent being based on the total weight of the hydrocarbon feedstock, including the aromatics and sulfur components thereof. The more applicable hydrocarbon feedstock aromatics concentration is in the range of from 2 wt. % to 30 wt. %, and, most applicable, the hydrocarbon feedstock aromatics concentration is from 3 wt. % to 20 wt. %.

The final catalyst composition of the invention may be employed as a part of any suitable reactor system that provides contacting the catalyst thereof with the hydrocarbon feedstock under suitable dearomatization or aromatics hydrogenation conditions that may include the presence of hydrogen and an elevated pressure and temperature. One preferred reactor system is that which includes a bed of the final catalyst composition contained within a reactor vessel equipped with a reactor feed inlet means, such as a feed nozzle, for introducing the hydrocarbon feedstock into the reactor vessel, and a reactor effluent outlet means, such as an effluent outlet nozzle, for withdrawing the reactor effluent or the product having a reduced aromatics concentration from the reactor vessel.

The amount of dearomatization provided by the inventive process generally exceeds 20 molar percent of the aromatics contained in the hydrocarbon feedstock. But, it is desirable for the inventive process to provide a molar percent dearomatization of the hydrocarbon feedstock that exceeds 40 molar percent. It is preferred for the inventive process to provide for a dearomatization of more than 50 molar percent, and, most preferred, more than 80 molar percent. The term molar percent dearomatization is used herein to mean the fraction of the moles of aromatics contained in the hydrocarbon feedstock that are saturated by the inventive process divided by the total moles of aromatics contained in the hydrocarbon feedstock. The molar percent dearomatization may be calculated by dividing the difference in the total moles of aromatics in the hydrocarbon feedstock and in the product by the total moles of aromatics in the hydrocarbon feedstock. Thus, the product of the inventive process will have a reduced aromatics concentration such that it contains an amount of aromatics that is not more than 80 molar percent of the aromatics contained in the hydrocarbon feedstock, but desirably, not more than 60 molar percent. It is preferred for the product to contain an amount of aromatics that is not more than 50 molar percent of the aromatics contained in the hydrocarbon feedstock, and, most preferred, not more than 20 molar percent.

When the inventive process is dearomatizing a refinery distillate stream as its hydrocarbon feedstock, the reaction pressure is generally in the range of from 10 bar (145 psi) to 100 bar (1470 psi), preferably from 20 bar (290 psi) to 70 bar (1028 psi), and, more preferably, from 30 bar (435 psi) to 60 bar (870 psi).

For the dearomatization of a hydrocarbon feedstock, the reaction temperature at which the hydrocarbon feedstock is contacted with the final catalyst composition is in the range of from 125° C. (247° F.) to 350° C. (662° F.), preferably, from 150° C. (302° F.) to 325° C. (617° F.), and, most preferably, from 175° C. (347° F.) to 300° C. (572° F.).

The flow rate at which the hydrocarbon feedstock is charged to the reaction zone of the inventive process is generally such as to provide a liquid hourly space velocity (LHSV) in the range of from 0.01 hr$^{-1}$ to 10 hr$^{-1}$. The term "liquid hourly space velocity," as used herein, means the numerical ratio of the rate at which the hydrocarbon feedstock is charged to the reaction zone of the inventive process in volume per hour divided by the volume of catalyst contained in the reaction zone to which the hydrocarbon feedstock is charged. The preferred LHSV is in the range of from 0.05 hr$^{-1}$ to 6 hr$^{-1}$, more preferably, from 0.1 hr$^{-1}$ to 4 hr$^{-1}$, and, most preferably, from 0.2 hr$^{-1}$ to 3 hr$^{-1}$.

The amount of hydrogen charged to the reaction zone of the inventive process can be greatly dependent upon the amount of aromatics contained in the hydrocarbon feedstock that is to be dearomatized. Generally, the amount of hydrogen relative to the amount of hydrocarbon feedstock charged to the reaction zone is in the range upwardly to 1781 m$^3$/m$^3$ (10,000 SCF/bbl). It is preferred for the hydrogen gas charge rate to be in the range of from 89 m$^3$/m$^3$ (500 SCF/bbl) to 1781 m$^3$/m$^3$ (10,000 SCF/bbl), more preferably, from 178 m$^3$/m$^3$ (1,000 SCF/bbl) to 1602 m$^3$/m$^3$ (9,000 SCF/bbl), and, most preferably, from 356 m$^3$/m$^3$ (2,000 SCF/bbl) to 1425 m$^3$/m$^3$ (8,000 SCF/bbl).

The following examples are presented to further illustrate certain aspects of the invention, but they are not to be construed as unduly limiting the scope of the invention.

EXAMPLE I

The descriptions in this Example I illustrate the preparation of the inventive, high macroporosity support composition containing an amorphous silica-alumina made by the pH swing method and the resulting aromatics hydrogenation catalyst using such support composition and the preparation of a conventional support containing conventionally made silica-alumina and the resulting catalyst using such conventional support.

Extrudate Formation. A mixture of silica-alumina powder and distilled water (mix LOI=64%) were placed in a Simpson muller and mulled for 105 minutes. "Superfloc A" extrusion aid was added at a level of 2% based on dry powder and the mix mulled for an additional 5 minutes. This material was then extruded through die inserts to give 1.6 mm trilobe pellets after drying at 275° F. for 3-4 hrs and calcining at 1000° F. for 2 hrs. The properties of the extrudates resulting from both the conventional and pH-swing silica-alumina powders are shown in Table 1 below.

TABLE 1

| Description | | Extrudate A | Extrudate B |
|---|---|---|---|
| Silica-alumina powder | | pH-swing | conventional |
| Total Hg intrusion volume | cc/g | 1.0411 | 0.9606 |
| Macroporosity (>350 Ang) | % | 62.4 | 38.0 |
| Hg pore volume 50-350 Ang | % | 35.41 | 50.0 |
| Hg pore volume 350-2000 Ang | % | 48.03 | 3.4 |
| Hg pore volume > 5000 Ang | % | 2.0 | 30.96 |
| Hg pore volume < 70 Ang | % | 6.29 | 45.94 |
| Median pore diameter (vol) | Ang | 600 | 74 |
| Median pore diameter (area) | Ang | 98 | 57 |
| Surface Area | m2/g | 253 | 395 |
| Water pore volume | cc/g | 0.988 | 1.05 |

Catalyst Preparation. A solution of tetraammine platinum nitrate and tetraammine palladium nitrate in dilute aqueous ammonia (solution pH~9.5) and at the concentrations needed to give the target Pt and Pd catalyst loading were impregnated using a pore volume saturation method onto the silica-alumina support. The wet impregnates were dried at 257° F. for 3 hrs and then calcined in air at 545° F. for 2 hrs. The catalysts were then tested for aromatics saturation activity. The results are shown in Table 2.

EXAMPLE II

This Example II illustrates the use of the catalyst compositions described in Example I in the dearomatization of hydrocarbon feedstock and presents performance data for the catalysts.

White Oil Test: Feed=heavy naphthenic white oil. UV abs @ 275 nm (0.5 cm cell)=77.71. Test conditions: Press=2175 psig, H$_2$/Oil=4600 SCF/bbl, LHSV=0.96, T=420° F.

Diesel Oil Test: Feed=hydrotreated distillate (N & S<1 ppm); aromatics by SFC=47.6 wt %. Test conditions: Press=600 psig, H$_2$/Oil=2500 SCF/bbl, LHSV=3.0, T=400° F.

Catalyst Activation: Catalysts were loaded into a fixed bed trickle phase reactor with SiC diluent (1:2 vol/vol catalyst/diluent) and treated under hydrogen at test gas rates and 300° F. for 3 hrs. The temperature was raised to 600° F. at 50 F./hr and held for 1 hr. The temperature was then lowered to 200° F. before the introduction of feed and establishment of testing conditions.

TABLE 2

Testing Results

| | Extrudate | wt % Pt | wt % Pd | white oil test abs @ 275 nm 0.5 cm cell | diesel test T (F.) for 80% aromatics conversion |
|---|---|---|---|---|---|
| Catalyst A1 | A | 0.3 | 0.5 | 0.092 | 350 |
| Catalyst A2 | A | 0.15 | 0.25 | 0.085 | NA |
| Catalyst B | B | 0.3 | 1.0 | 0.40 | 390 |

The results presented in Table 2 show that the aromatics hydrogenation catalyst prepared using the high macroporosity support composition (i.e., Catalyst A1 and Catalyst A2) exhibited superior hydrogenation activity to that of the catalyst using the conventional support.

That which is claimed is:

1. A composition, comprising: a support composition having a macroporosity greater than 51%, a surface area in the range of from 150 m$^2$/gm to 400 m$^2$/gm and comprising amorphous silica-alumina, wherein said amorphous silica-alumina has a silica content in the range of from 10 to 90 weight percent and an alumina content in the range of from 10 to 90 weight percent, and wherein said amorphous silica-alumina exhibits the characteristic of a strong aluminum NMR penta-coordinated peak representing greater than 30% of the aluminum of said amorphous silica-alumina.

2. A composition as recited in claim 1, wherein said support composition has a mesoporostiy greater than 30%.

3. A composition as recited in claim 2, wherein the percentage of the total pore volume of said support composition contained in its macropores having a pore diameter in the range of from 350 Å to 2000 Å is greater than 40%.

4. A composition as recited in claim 3, wherein the percentage of the total pore volume of said support composition contained in the macropores having a pore diameter greater than 5000 Å is less than 4%.

5. A composition as recited in claim 4, wherein the percentage of the total pore volume of said support composition contained in the smaller pores having a pore diameter of less than 70 Å is less than 10%.

6. A composition as recited in claim 5, wherein said amorphous silica-alumina has an A/B ratio exceeding 2.2, wherein A is the pore volume contained in the pores of said amorphous silica-alumina having a pore diameter less than 2150 Å, and B is the pore volume contained in the pores of said amorphous silica-alumina having a pore diameter of less than 210 Å.

7. A composition as recited in claim 6, further comprising: a noble metal selected from the group consisting of platinum, palladium and a combination thereof.

8. A composition as recited in claim 7, wherein said amorphous silica-alumina is prepared by a pH swing method.

9. A composition as recited in claim 8, wherein said noble metal is present in said composition in an amount in the range of from 0.01 wt. % to 5 wt. % with the weight percent being based on the total weight of said composition and calculated as elemental metal.

10. A composition as recited in claim 9, wherein said noble metal includes both palladium and platinum present in said composition in amounts such that the weight ratio of elemental palladium-to-platinum is in the range of from 1:10 to 10:1.

11. A composition as recited in claim 10, wherein said composition has a total surface area that is in the range of from 200 m²/gm to 350 m²/gm.

12. A composition as recited in claim 6, wherein the A/B ratio exceeds 2.4.

13. A composition as recited in claim 1, wherein said support composition has a mesoporostiy greater than 35%.

14. A composition as recited in claim 6, wherein the A/B ratio exceeds 2.5.

15. A composition as recited in claim 13, wherein said support composition has a mesoporostiy greater than 40%.

* * * * *